(12) United States Patent
Rathjen

(10) Patent No.: US 8,747,395 B2
(45) Date of Patent: Jun. 10, 2014

(54) DEVICE FOR TREATING EYE TISSUE

(75) Inventor: Christian Rathjen, Bremen (DE)

(73) Assignee: Ziemer Holding AG (CH)

( * ) Notice: Subject to any disclaimer, the term of this patent is extended or adjusted under 35 U.S.C. 154(b) by 1081 days.

(21) Appl. No.: 12/356,279

(22) Filed: Jan. 20, 2009

(65) Prior Publication Data

US 2009/0187174 A1    Jul. 23, 2009

(30) Foreign Application Priority Data

Jan. 21, 2008  (EP) .................................... 08405021

(51) Int. Cl.
*A61B 17/22* (2006.01)

(52) U.S. Cl.
USPC ................................ 606/5; 351/200; 351/210

(58) Field of Classification Search
CPC .... A61F 9/008; A61F 9/00825; A61F 9/0084
USPC ......... 606/4, 5, 10, 17, 18; 351/200, 210, 221
See application file for complete search history.

(56) References Cited

U.S. PATENT DOCUMENTS

| | | | | |
|---|---|---|---|---|
| 2,765,702 | A * | 10/1956 | Sachtleben | 351/205 |
| 6,268,958 | B1 * | 7/2001 | Furuhashi | 359/381 |
| 6,437,911 | B1 * | 8/2002 | Hasegawa | 359/381 |
| 6,899,707 | B2 * | 5/2005 | Scholler et al. | 606/5 |
| 7,597,444 | B2 * | 10/2009 | Rathjen et al. | 351/221 |
| 7,618,415 | B2 * | 11/2009 | Kessler et al. | 606/10 |
| 2002/0099363 | A1 * | 7/2002 | Woodward et al. | 606/5 |
| 2004/0262522 | A1 * | 12/2004 | Kitahara et al. | 250/341.8 |
| 2006/0045327 | A1 | 3/2006 | Dang et al. | |
| 2007/0282312 | A1 | 12/2007 | Rathjen | |

FOREIGN PATENT DOCUMENTS

| | | |
|---|---|---|
| DE | 20 2004 013136 | 7/2005 |
| EP | 1 486 185 | 12/2004 |
| EP | 1 731 120 | 12/2006 |
| JP | H08-179218 | 7/1996 |
| JP | H09-198677 | 7/1997 |
| JP | 2003-199782 | 12/2001 |

OTHER PUBLICATIONS

European Search Report, dated Jul. 4, 2008, issued in corresponding European Application No. 08405021.0.

* cited by examiner

*Primary Examiner* — Victor Nguyen
(74) *Attorney, Agent, or Firm* — Ostrolenk Faber LLP

(57) ABSTRACT

An ophthalmological device (1) includes an optical transmission system (5) for transmitting femtosecond laser pulses (L) onto a projection lens (3) for projection onto or into the eye tissue (21). The device (1) also includes a lens interchange device (4) designed for interchanging and connecting different projection lenses (3) to the optical transmission system (5). The lens interchange device (4) includes a number of different projection lenses (3) which are connected mechanically to one another and which can be fed to the optical transmission system (5) by a rotational or translational movement in order to connect the former to the optical transmission system (5). The lens interchange device (4) makes it possible for a user to flexibly and efficiently change the projection lens (3) so that the projection lens (3) can be changed or altered without great expenditure of time and without using a varifocal lens, even between different applications and treatment steps.

12 Claims, 4 Drawing Sheets

DEVICE FOR TREATING EYE TISSUE

FIELD OF THE INVENTION

The present invention relates to a device for treating eye tissue by means of femtosecond laser pulses. The present invention relates in particular to a device for treating eye tissue, which comprises an optical transmission system for transmitting femtosecond laser pulses onto a projection lens for projecting the femtosecond laser pulses onto or into the eye tissue.

BACKGROUND OF THE INVENTION

Presently, sight defects such as myopia (short-sightedness), hyperopia (far-sightedness or long-sightedness) or astigmatism can be corrected permanently by means of refractive-surgical treatment. Refractive-surgical treatments are surgical procedures on the eye which change the optical refractive power of the eye with the aim of approximating it as closely as possible to a desired value. These days, laser technology is typically used for treating eye tissue, e.g. for tissue cuts and tissue reduction. In particular, highly focused femtosecond laser pulses with pulse widths of typically 100 fs to 1000 fs (1 fs=$10^{-15}$ s) are used for the tissue treatment. The cornea of the eye is currently treated using commercial femtosecond laser systems. However, since other tissue parts and tissue regions of the eye, such as the sclera, lens and retina, are also treated with the laser pulses, different working distances and hence focal distances are required for the different areas of application; this requires not only mechanical positioning mechanisms but also different light projection optics. Additionally, different applications and treatment regions often also require image fields (i.e. image regions in focus) with differing size and/or curvature, which in turn can be achieved by means of corresponding application-specific projection optics. In order to obtain different, application-specific focal diameters, focal shapes and focal extents in the projection direction and/or beam divergences, different projection optics with respectively different numerical aperture (NA) must likewise be used. Finally, different projection optics, in particular transparent application elements such as contact bodies, e.g. applanation bodies or distance bodies, may be required due to the specific optical properties of patient interfaces to be implemented. Flexible adaptation of the projection optics to the different application-specific demands could in an ideal case be made possible by a suitable varifocal lens.

Generally, a high NA is desirable because high NA allows the generation of small focal points (spot size), and hence a smaller cut-zone per pulse. It is actually very difficult to produce varifocal lenses which cover a large work region as a result of the often desired high NA, short working distances and in general very small focal sizes (spot sizes). If, additionally, a weight which is as low as possible and a small overall size are decisive (this can easily be the case for use on the eye with a small working distance), then the construction of suitable varifocal lenses is made even more difficult. Image fields with different curvature cannot be implemented by varifocal lenses known from the prior art. Since, for example, the retina and the cornea have a different curvature, different image field curvatures are also necessary.

SUMMARY OF THE INVENTION

It is an object of the present invention to propose a device for treating eye tissue by means of femtosecond laser pulses, in particular with femtosecond laser pulses, which does not have the disadvantages of the prior art. In particular, it is an object of the present invention to propose a device for treating eye tissue by means of femtosecond laser pulses, which enables a flexible adaptation of the projection optics to different demands without having to use complex varifocal lenses for this purpose. It is in particular a further object of the present invention to propose a device for treating eye tissue by means of femtosecond laser pulses, which enables a flexible adaptation of the projection optics to different requirements of focal length (focal distance), image field size, image field curvature, numerical aperture, focal diameter, focal shape, focal extent in the projection direction and beam divergence.

In accordance with the present invention, these objects are achieved in particular by the elements of the independent claims. Moreover, further advantageous embodiments emerge from the dependent claims and the description.

The device for treating eye tissue by means of femtosecond laser pulses comprises an optical transmission system for transmitting the femtosecond laser pulses onto a projection lens designed to project the femtosecond laser pulses onto or into the eye tissue.

The abovementioned objects are achieved by the present invention in particular by virtue of the fact that the device for treating eye tissue by means of femtosecond laser pulses additionally comprises a lens interchange device designed for interchanging and connecting the projection lens to the optical transmission system. The lens interchange device makes it possible to adapt a laser-based, opthalmological device to new applications without having to undertake large alterations or use complex varifocal lenses. The lens interchange device makes it possible for the user to flexibly and efficiently change the projection lens so that the projection lens can also be changed between different applications and treatment steps without great expenditure of time. In particular, the lens interchange device makes it possible to later adapt the system to new applications which were not yet known or conventional at the time of production of the opthalmological device. Compared to using varifocal lenses, the interchange of projection lenses additionally has the advantage that a controlled setting of lens parameters is not necessary, and hence the components and modules for parameter feedback and control associated therewith are dispensed with.

In a preferred embodiment alternative, the lens interchange device comprises a number of different projection lenses which are connected mechanically to one another, and the lens interchange device is designed to feed one of the projection lenses to the optical transmission system in order to connect the former to the optical transmission system. By way of example, the projection lenses differ in their focal length, image field size, image field curvature, numerical aperture, focal diameter, focal shape, focal extent in the projection direction and/or beam divergence. In different embodiment alternatives, the lens interchange device is designed to interchange the projection lenses by rotational movements or translational movements, with respectively one of the projection lenses being fed to the optical transmission system in order to connect the former to the optical transmission system by a rotational movement or a translational movement. A lens interchange device with a number of projection lenses affords the possibility of a particularly efficient change by means of simple manipulation without this necessitating attaching new projection lenses to the opthalmological device during the treatment.

In further embodiments, the projection lenses each comprise an application element to apply the projection lens to an eye, and/or the device comprises a common application element to apply the projection lens to an eye, with the lens interchange device being designed to combine the respective projection lens and the application element when one of the projection lenses is connected to the optical transmission system. The alternative with a number of application elements respectively attached to the projection lenses has the advantage that different application elements, for example with a different contact shape or working distance, can also be interchanged by simple manipulation and independently of the projection lens. In a combined embodiment, it is possible that both different application elements and/or projection lenses are introduced, and that a common application element is provided, which is used to attach them to the eye, for example.

In a further embodiment alternative, the lens interchange device comprises a connection module for the removable holding and connection of the projection lens to the optical transmission system. Combining the connection module with a lens interchange device for a number of projection lenses makes it possible, as preparation for a treatment, to equip the lens interchange device with projection lenses and/or application elements which are suitable specifically for the application and/or the patient, and then introduce these during the treatment by means of a rotational movement or translational movement without further manipulation. A lens interchange device with only one connection module makes possible a device which permits inserting and interchanging different projection lenses during the treatment and which is designed in a particularly simple manner.

The optical transmission system is preferably designed to feed the femtosecond laser pulses to the projection lens as substantially parallel beams. Entry rays which enter the projection lens in parallel have the advantage that imprecision during the mechanical introduction of different projection lenses (installation tolerances) has no effect on the focal length obtained by the projection lens.

In one embodiment alternative, the device comprises a measurement system for determining the position of the projection lens connected to the optical transmission system relative to the device. The measurement system makes it possible to detect, display and/or correct imprecisely positioned projection lenses.

In a further embodiment alternative, the device comprises a detector for determining a lens type identifier provided for the projection lens connected to the optical transmission system. The detector is preferably connected to a laser control module and is designed to transmit the lens type identifier of the projection lens connected to the optical transmission system to the laser control module. By way of example, the lens type identifier is designed as a mechanical, optical, electrical or wireless identifier. By assigning and identifying a lens type, it is possible to control the laser beam in terms of its state, transmission, alignment and/or deflection as a function of the optical properties of the projection lens used.

BRIEF DESCRIPTION OF THE DRAWINGS

In the following text, one embodiment of the present invention will be described on the basis of an example. The exemplary embodiment is illustrated by the following attached figures.

DETAILED DESCRIPTION OF THE PREFERRED EMBODIMENTS

Figures 1A, 1B:
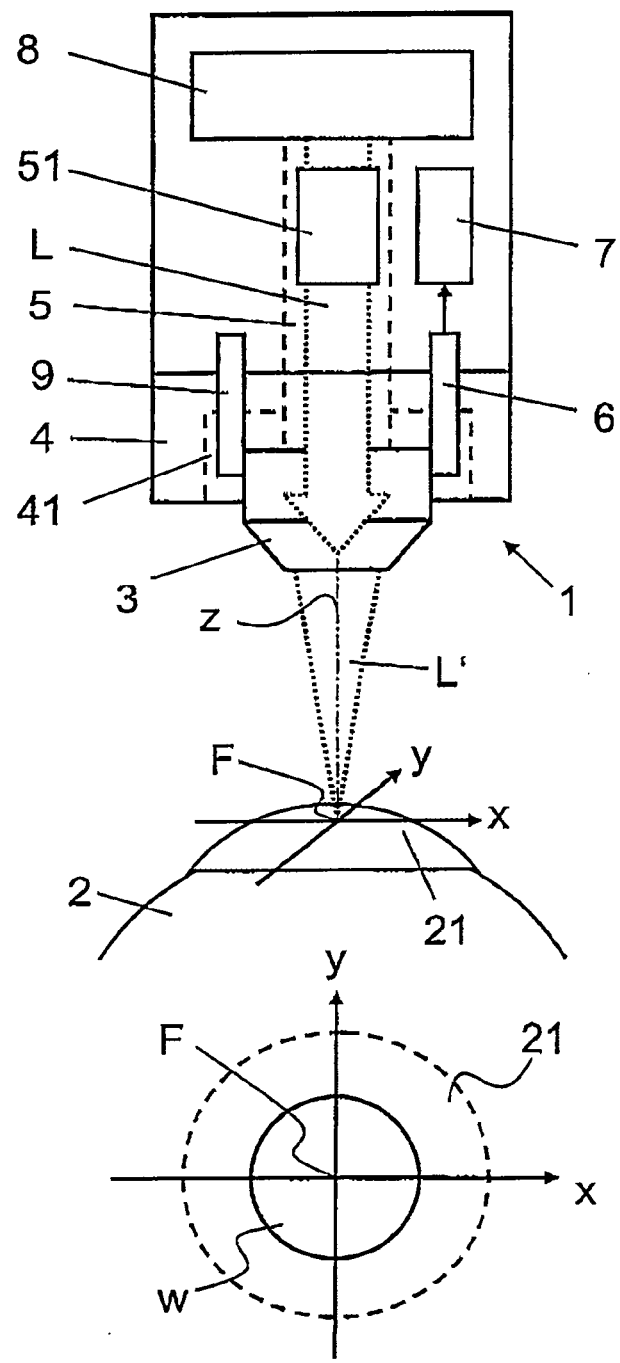
FIG. 1a shows a block diagram which schematically illustrates an opthalmological device for treating eye tissue by means of femtosecond laser pulses.
FIG. 1b shows a top view of a treatment area in the eye tissue which is treated by the opthalmological device.

In FIGS. 1a, 2, 3, 4a, 4b and 4c, the reference symbol 1 designates an opthalmological device, or an opthalmological device arrangement, having a laser source 8 and an optical transmission system 5 which optically connects the laser source 8 to an (optical) projection lens 3 for the purpose of focused projection of laser pulses. In particular, the laser source 8 comprises a femtosecond laser for generating a laser beam L with femtosecond laser pulses having pulse widths of typically 10 fs to 1000 fs (1 fs=$10^{-15}$ s). The laser source 8 is arranged in a separate housing or in a housing shared with the projection lens 3. The projection lens 3 projects a focused pulsed laser beam L' for punctiform tissue disintegration at a focus F onto or inside the eye tissue 21, for example onto or into the cornea. As will be described in more detail below, the opthalmological device 1 in the embodiment alternatives in accordance with FIGS. 2, 3, 4a, 4b and 4c comprises a number of (inter-)changeable projection lenses 3, 3'.

The transmission system 5 comprises a number of optical elements such as lenses, apertures, deflection mirrors and optical waveguides in order to feed the femtosecond laser pulses from the laser source 8 to the connected projection lens 3. The transmission system 5 is preferably designed to feed the laser beams L in a substantially parallel fashion to the projection lens 3; this is not the case in interchangeable lenses known from photography, for example. Furthermore, as illustrated schematically in FIG. 1a, the optical transmission system 5 comprises a deflection module 51, i.e. an optical scanner module designed to deflect the femtosecond laser pulses generated by the laser source 8 in at least one direction and hence move the focus F of the pulsed laser beam L' in at least one direction x, y of the (contiguous or non-contiguous) defined treatment area w in the tissue 21 of the eye 3 in accordance with a scan pattern. The deflection module 51 is arranged (e.g. together with the laser source 8) in a separate housing or in a housing shared with the projection lens 3 or lens interchange device 4. In one embodiment alternative, the optical transmission system 5 and/or the projection lens 3 comprise or comprises moveable lenses in order to also adjust the focus F of the pulsed laser beam L' in the normal direction to the x/y directions (for example along the optical axis z). Depending on the embodiment alternative, the opthalmological device 1 additionally optionally comprises a drive module in order to move the projection lens 3, and hence the focus F, along the x and/or y and/or normal directions.

Here, for the purpose of an improved understanding, reference is intended to be made to the fact that FIGS. 1a, 2, 3, 4a, 4b and 4c illustrate the opthalmological device 1 schematically and in a simplified manner. For example, the figures do not precisely reproduce the fact that the projection lenses 3, 3' have a high numerical aperture of, for example, at least 0.3.

In FIG. 1a, the reference symbol 4 designates a lens interchange device for interchanging and connecting the projection lens 3 to the optical transmission system 5. Different embodiments of the lens interchange device 4 are illustrated in FIGS. 1a, 2, 3, 4a, 4b and 4c.

In the embodiment in accordance with FIG. 1a, the lens interchange device 4 comprises a connection module 41 for removably inserting, holding and connecting the projection lens 3 to the optical transmission system 5. By way of example, the connection module 41 comprises a threaded or bayonet cap for holding and attaching the projection lens 3 to the opthalmological device 1. In the attached state, the projection lens 3 is connected optically to the optical transmission system 5.

In the embodiments in accordance with FIGS. 2, 3, 4a, 4b and 4c, the lens interchange device 4, 4a, 4b in each case comprises a number of different projection lenses 3, 3' which are connected mechanically to one another. The projection lenses 3, 3' are in each case provided with a lens type identifier and differ from one another by their optical properties such as numerical aperture, focal length, image field size, image field curvature, focal diameter, focal shape, focal extent in the projection direction and/or beam divergence.

Figure 2:
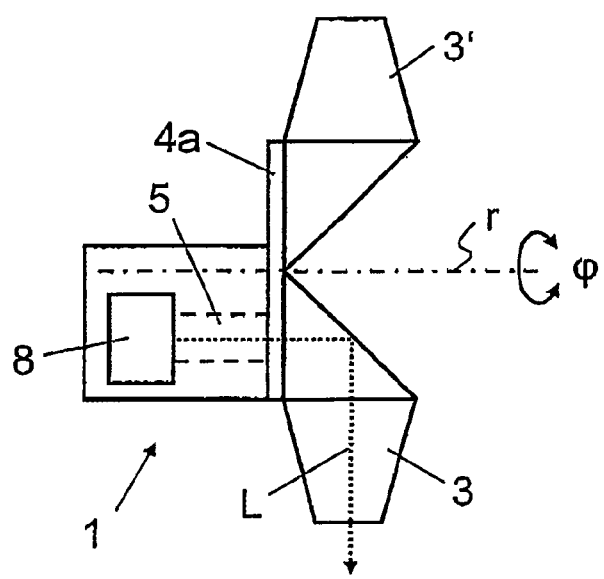
FIG. 2 shows a block diagram which in a side view schematically illustrates an embodiment alternative of the opthalmological device with a number of mechanically connected projection lenses.

In the embodiment in accordance with FIG. 2, the lens interchange device 4a is designed to interchange the projection lenses 3, 3' by means of rotational movements φ about a rotational axis r. The lens interchange device 4a comprises a carrier which can rotate about the rotational axis r and onto which the projection lenses 3, 3' are attached. The lens interchanged device 4a is for example designed in the form of revolving optics. A selected projection lens 3, 3' is fed to the optical transmission system 5 by means of a rotational movement φ, and it is connected optically to the optical transmission system 5.

Figure 3:
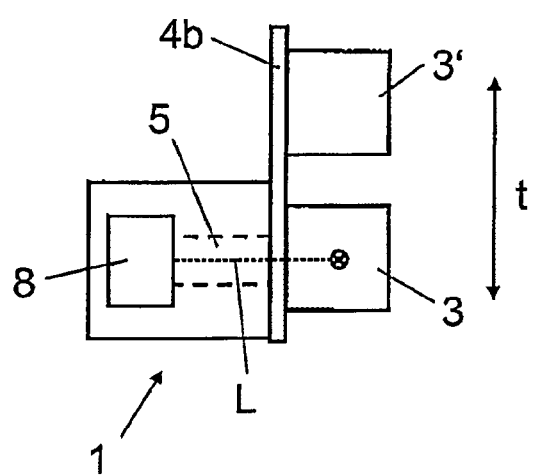
FIG. 3 shows a block diagram which in a top view schematically illustrates a further embodiment alternative of the opthalmological device with a number of mechanically connected projection lenses.

In the embodiment in accordance with FIG. 3, the lens interchange device 4b is designed to interchange the projection lenses 3, 3' by means of translational movements t. The lens interchange device 4b comprises a carrier skid which can be displaced along an axis and on which the projection lenses 3, 3' are attached. A selected projection lens 3, 3' is fed to the optical transmission system 5 by means of a translational movement t, and it is connected optically to the optical transmission system 5.

When being connected to the optical transmission system 5, the selected projection lens 3 is preferably fixed in the rotation or translation, for example mechanically by means of a latching or stop mechanism.

In one alternative, the carrier of the lens interchange device 4a, 4b has one or more connection modules for removably holding respectively one projection lens 3, 3', as described in connection with FIG. 1a. As a result, it is possible to equip the lens carrier with different sets of projection lenses 3, 3' which for example are provided for different treatment steps and applications during a treatment of a patient.

As illustrated schematically in FIG. 1a, the opthalmological device 1 comprises a detector 6 for detecting the lens type identifier of the connected projection lens 3. The lens type identifier is designed, for example, as a mechanical, optical, electrical or wireless identifier and specifies a type code assigned to the lens type. In accordance with the embodiment of the lens type identifier, the detector 6 comprises a sensor for detecting and reading a mechanically designed identifier (e.g. a code formed by structured elements); for detecting an optically designed identifier (e.g. a bar code or a screen code); for reading an electrically designed identifier (e.g. a capacitive or ohmic code); or for receiving and identifying a wireless identifier (e.g. using RFID (radio frequency identification)).

The detector 6 is connected to a laser control module 7, designed as a programmed logic module by means of software and/or hardware, and said detector is designed to transmit the determined lens type identifier to the laser control module 7. The laser control module 7 is connected to the deflection module 51 and the laser source 8 for the purpose of transmitting control signals (control commands, control programs). The laser control module 7 is arranged in a separate housing or in a housing shared with the lens interchange device 4. The laser control module 7 comprises physical nominal values, respectively assigned to the different lens types, which specify optical properties of the respective lens type, e.g. numerical aperture, focal length, image field size, image field curvature, focal diameter, focal shape, focal extent in the projection direction and/or beam divergence, and/or assigned control program modules. On the basis of the detected lens type identifier, the laser control module 7 is designed to control the laser source 8 and the optical transmission system 5, in particular the deflection module 51, by transmitting control commands from the assigned control program modules and/or as a function of the assigned physical nominal values to the laser source 8, the deflection element 51 and/or other controllable elements of the optical transmission system 5, such as displaceable lenses and controllable apertures. Hence, the laser beam L of the laser source 8 is, depending on the used lens type, automatically changed and altered in terms of, for example, its energy, pulse rate and/or pulse width, and its transmission, alignment and deflection properties.

In FIG. 1a, the reference symbol 9 designates a measurement system for determining the position of the projection lens connected to the optical transmission system 5 relative to the opthalmological device 1 and, in particular, relative to the optical transmission system 5. In different embodiment alternatives, the measurement system 9 is designed to determine the mechanical relative position in a capacitive, inductive, ohmic or optical manner. The measurement system 9 is connected to the laser control module 7 and designed to transmit the determined relative position to the laser control module 7. Depending on the embodiment alternative, the laser control module 7 shows a deviation of the relative position from a defined tolerance range to the user by means of a user interface, e.g. acoustically and/or optically, and/or adapts the control of the laser source 8 and/or the optical transmission system 5, in particular the deflection module 51, in accordance with the deviation from a defined reference position.

Although this is not explicitly illustrated in the simplified FIGS. 2, 3, 4a, 4b and 4c, the opthalmological device 1 illustrated in these figures also comprises, in corresponding embodiment alternatives, a laser control module 7 and a detector 6 and/or a measurement system 9 for determining the type or position, and for controlling the laser beam L based on this.

Figure 4A:
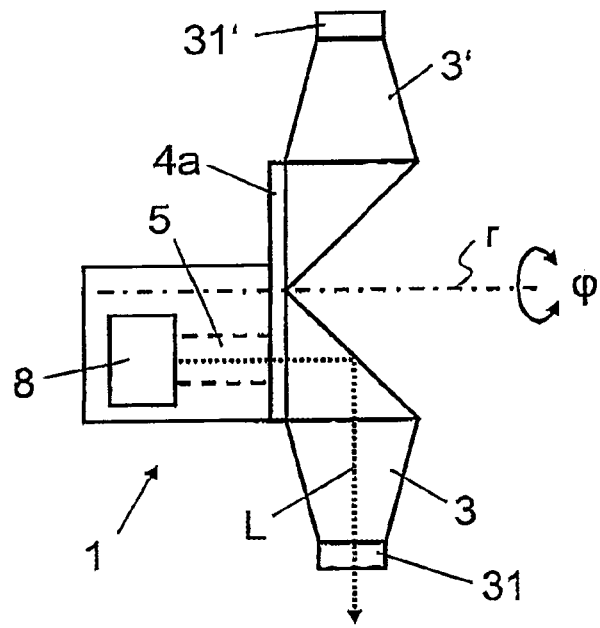
FIG. 4a shows a block diagram which schematically illustrates a further embodiment alternative of the opthalmological device with a number of application elements, each attached to one of the projection lenses.
Figure 4B:
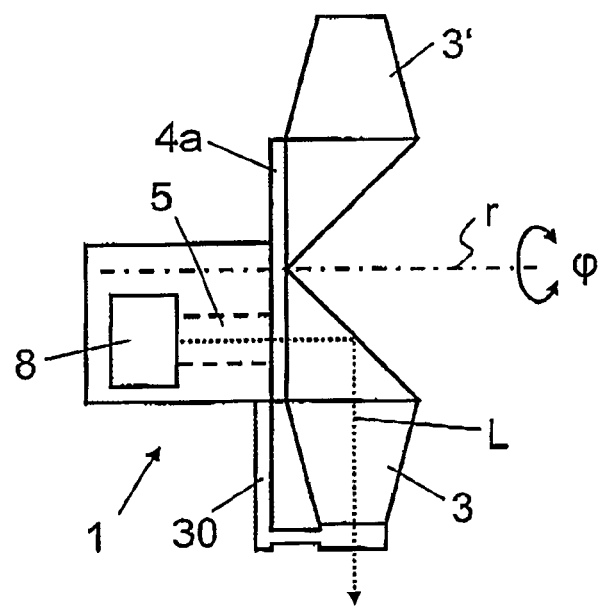
FIG. 4b shows a block diagram which schematically illustrates a further embodiment alternative of the opthalmological device with an application element common to a number of projection lenses.
Figure 4C:
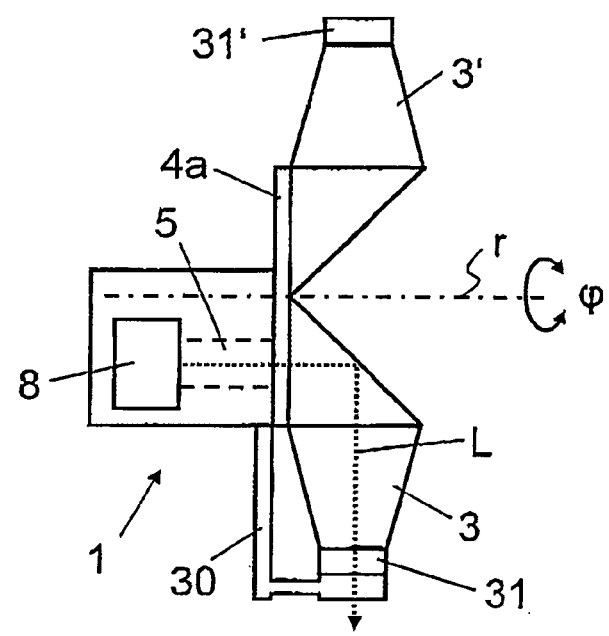
FIG. 4c shows a block diagram which schematically illustrates a combined embodiment alternative of the opthalmological device with a number of application elements attached to the projection lenses and a further common application element.

FIGS. 4a, 4b and 4c show embodiment alternatives in which the opthalmological device 1 is provided with one or more application elements 30, 31, 31'. By way of example, the application elements 30, 31, 31' comprise contact bodies, e.g.

applanation bodies, which are transparent at least in places and/or in part, or concave/convex moulds. Depending on the embodiment alternative, the application elements 30, 31, 31' additionally comprise a suction ring, or different attachment devices, for fixing them to the eye 2.

In the embodiment in accordance with FIG. 4a, the application elements 31, 31' are each attached fixedly or interchangeably to the projection lenses 3, 3' and can, for example, be designed differently, e.g. an applanation body, a concave mould or different distance bodies for different treatment steps and/or with, without or differing attachment means for fixing them to the eye 2.

In the embodiment in accordance with FIG. 4b, the opthalmological device 1 is provided with a combined fixed or interchangeable application element 30, and the lens interchange device 4 is designed and arranged such that the different projection lenses 3, 3' can be changed so that, in the state where they are connected to the optical transmission system 5, they can be combined contactlessly or in a manner mechanically contacting the application element 30.

The embodiment in accordance with FIG. 4c is a combination of the embodiments in accordance with FIGS. 4a and 4b, with on the one hand respectively different application elements 31, 31' being attached to the projection lenses 3, 3', and, on the other hand, a combined application element 30 being provided on the opthalmological device 1. In the combined embodiment in accordance with FIG. 4c it is possible, one the one hand, to select and introduce different projection lenses 3, 3' and/or application elements 31, 31' during a treatment and, on the other hand, it is possible to keep a common application element 30 during the treatment, for example a suction ring to attach them to the eye 2, a distance body and/or a protective aperture.

Although this is not illustrated, it is also possible to combine the application elements 30, 31, 31' with the embodiments in accordance with FIGS. 1a and 3.

In a further embodiment alternative, the lens interchange device 4, 4a, 4b additionally comprises an optional drive module for the motorized change of the projection lenses 3, 3' and/or the application elements 31, 31'.

The invention claimed is:

1. A device for treating eye tissue by means of femtosecond laser pulses, comprising:
    an optical transmission system for transmitting the femtosecond laser pulses onto a projection lens for projecting the femtosecond laser pulses onto or into the eye tissue,
    a lens interchange device designed for interchanging and connecting the projection lens to the optical transmission system, and
    a detector for determining a lens type identifier provided for the projection lens connected to the optical transmission system, the lens type identifier indicating for the projection lens a type of lens from different types of projection lenses having different optical properties, the optical properties including at least one of: focal length, image field size, image field curvature, numerical aperture, focal diameter, focal shape, focal extent in the projection direction, and beam divergence.

2. The device according to claim 1, wherein the lens interchange device comprises a number of different projection lenses which are connected mechanically to one another, and the lens interchange device is designed to feed one of the projection lenses to the optical transmission system in order to connect the former to the optical transmission system.

3. The device according to claim 2, wherein the lens interchange device is designed to interchange the projection lenses by rotational movements, with respectively one of the projection lenses being fed to the optical transmission system in order to connect the former to the optical transmission system by a rotational movement.

4. The device according to claim 2, wherein the lens interchange device is designed to interchange the projection lenses by translational movements, with respectively one of the projection lenses being fed to the optical transmission system in order to connect the former to the optical transmission system by a translational movement.

5. The device according to claim 2, wherein the projection lenses each comprise an application element to apply the projection lens to an eye.

6. The device according to claim 2, wherein the device comprises an application element to apply the projection lens to an eye, and the lens interchange device is designed to combine the respective projection lens and the application element when one of the projection lenses is connected to the optical transmission system.

7. The device according to claim 1, wherein the lens interchange device comprises at least one connection module for removably holding and connecting the projection lens to the optical transmission system.

8. The device according to claim 1, wherein the optical transmission system is designed to feed the femtosecond laser pulses to the projection lens as substantially parallel beams.

9. The device according to claim 1, wherein the detector is connected to a laser control module, and the detector is designed to transmit the lens type identifier of the projection lens connected to the optical transmission system to the laser control module.

10. The device according to claim 1, wherein the lens type identifier is designed as one selected from the group consisting of a mechanical, an optical, an electrical and a wireless identifier.

11. The device according to claim 1, further comprising a measurement system for determining the position of the projection lens connected to the optical transmission system relative to the device.

12. A device for treating eye tissue with femtosecond laser pulses, comprising:
    an optical transmission system for transmitting the femtosecond laser pulses onto a projection lens for projecting the femtosecond laser pulses onto or into the eye tissue,
    a lens interchange device designed for interchanging and connecting the projection lens to the optical transmission system, and
    a detector for determining a lens type identifier provided for the projection lens connected to the optical transmission system, wherein the detector is connected to a laser control module, the detector is designed to transmit the lens type identifier of the projection lens connected to the optical transmission system to the laser control module, and the lens type identifier indicating for the projection lens a type of lens from different types of projection lenses having different optical properties, the optical properties including at least one of: focal length, image field size, image field curvature, numerical aperture, focal diameter, focal shape, focal extent in the projection direction, and beam divergence.

* * * * *